(12) United States Patent
Yang

(10) Patent No.: US 6,330,819 B1
(45) Date of Patent: Dec. 18, 2001

(54) METHOD AND APPARATUS FOR CALIBRATING A DISSOLVED OXYGEN ANALYZER

(75) Inventor: Feng-Yi Yang, Taipei (TW)

(73) Assignee: Taiwan Semiconductor Manufacturing Company, Ltd, Hsin Chu (TW)

( * ) Notice: Subject to any disclaimer, the term of this patent is extended or adjusted under 35 U.S.C. 154(b) by 0 days.

(21) Appl. No.: 09/412,208

(22) Filed: Oct. 5, 1999

(51) Int. Cl.[7] ................................................. G01N 27/26
(52) U.S. Cl. .......................... 73/1.03; 73/1.06; 73/1.07; 73/1.88
(58) Field of Search ...................... 73/1.02, 1.03, 73/1.06, 1.07, 1.88, 19.01, 19.1; 204/415, 412

(56) References Cited

U.S. PATENT DOCUMENTS 4,207,161 * 6/1980 Pegnim ................................ 204/408
4,427,772 * 1/1984 Kodera et al. ....................... 204/403
4,435,268 * 3/1984 Martin et al. ....................... 204/408
5,589,133 * 12/1996 Suzuki .................................. 422/79

FOREIGN PATENT DOCUMENTS 56-22947 * 3/1981 (JP) ..................................... 205/120
02-293658 * 12/1990 (JP) ..................................... 73/1.03

* cited by examiner

Primary Examiner—Daniel S. Larkin
(74) Attorney, Agent, or Firm—Tung & Associates

(57) ABSTRACT

A method and an apparatus for calibrating a dissolved oxygen analyzer are disclosed. In the method, a zero point is first determined and set on the analyzer by filling into the analyzer a saturated aqueous solution of an oxidizer that contains 0 ppb oxygen. A span point is then set on the analyzer by filling a sample solution in the analyzer and flowing a cell current through a Faraday electrode until a 20 ppb oxygen is produced and then setting the point as a span point for completing a two-point calibration process. A slope for calibration can be obtained between the zero point and the span point.

10 Claims, 2 Drawing Sheets

METHOD AND APPARATUS FOR CALIBRATING A DISSOLVED OXYGEN ANALYZER

FIELD OF THE INVENTION

The present invention generally relates to a method and an apparatus for calibrating a dissolved oxygen analyzer and more particularly, relates to a method and an apparatus for automatically calibrating a dissolved oxygen analyzer by first setting a zero point on the analyzer with an oxidizer solution that contains 0 ppb oxygen and then setting a span point on the analyzer on a sample solution during an electrolysis reaction until 20 ppb oxygen is produced. A suitable oxidizer solution used can be a saturated aqueous solution of sodium sulfite.

BACKGROUND OF THE INVENTION

Large quantities of ultrapure water or deionized (DI) water are consumed in the fabrication of IC devices, for instance, in a large number of wet cleaning and wet bench processes. The consumption of ultrapure water and DI water increases with the ever increasing wafer size. The DI water tank required for a 200 mm wafer wet bench is twice as large as one required for a 150 mm wafer wet bench. The consumption of water in a 200 mm wafer fab plant is therefore doubled from that of a 150 mm fab plant.

Many contaminants exist in a raw water supply. These include particles, organic materials, inorganic materials, microorganisms, bacteria and dissolved gases which include oxygen. When a raw water supply is fed through an ultrapure or DI water generating system, the contaminants are sequentially removed by a series of different types of filters, degassifiers, and ion-exchanger units.

When ultrapure water or DI water is used in the processing of IC wafers, one of the most critical impurities contained in water is the dissolved oxygen content. It is desirable that the dissolved oxygen in water to be kept as low as possible in order to prevent the growth of native oxide on bare silicon surfaces. This is normally achieved by making improvements in the performance of vacuum degassifiers. For instance, three popular degassification processes have been designed which include the hot water process that involves heating DI water to a temperature over 55° C.; the nitrogen purging process which includes injecting a nitrogen flow into a DI water container; and a catalytic process which involves contacting DI water with a palladium compound contained in a vessel. It has been determined in semiconductor processing that it is generally desirable to keep the dissolved oxygen level under 100 ppb, and preferably under 50 ppb.

The ability to accurately monitor the content of dissolved oxygen in ultrapure water or DI water is therefore an important aspect of an IC wafer fabrication process. Presently, a commercially available dissolved oxygen analyzer is only capable of detecting the content of dissolved oxygen in water and performing a verification function, but not automatically calibrating itself. While it is not known, other than the growth of native oxide on bare silicon surfaces, the other detrimental effects of oxygen content in water, it is nevertheless agreed that the dissolved oxygen content in ultrapure water or DI water should be kept at a minimum, i.e., at a concentration of not higher than 50 ppb in order to minimize the potential detrimental effects.

Presently, since there is no standard calibration solution available for calibrating a dissolved oxygen analyzer, the analyzer is calibrated in atmosphere or by an air calibration method. A typical calibration curve is shown in FIG. 1. The air calibration method must be carried out manually. A sample flow is first shut off and an oxygen electrode is taken out of the flow cell and exposed to atmosphere until a stable reading in % saturation is obtained. For instance, the on-line reading is expressed by:

$$O_2[\% \text{ sat}] = \text{cell current/calibration slope}$$

While the calibration slope is calculated by the ratio of:

$$\text{slope} = \text{cell current at 100\% sat.}/100\% \text{ sat value}$$

$$O_2[\text{ppb}] = \text{correction factor} \times O_2[\% \text{ sat.}]$$

In the conventional calibration method shown above, the reading is zeroed when no cell current is flown through the analyzer. However, this is not an absolute zero calibration. Moreover, when an oxygen electrode is exposed to a high concentration of oxygen, the silver anode discharges a large electrical current such that silver oxide film is readily formed on the anode surface which leads to a short lifetime of the silver electrode.

The conventional calibration method is sometimes supplemented by a Faraday verification procedure when the oxygen concentration of the sample is below 200 ppb. Periodically, a voltage is applied to the Faraday electrode to induce electrolysis in the sample solution and the formation of molecular oxygen and hydrogen. Based on Faraday's law and the measured flow rate, the current passing the electrodes can be adjusted automatically to produce an addition of approximately 20 ppb of oxygen. This is calibrated as a span point in a two-point calibration process. Since the oxygen electrode's response is perfectly linear to the oxygen concentration changes, the resulting electrode slope can be calculated with a single addition of oxygen.

As shown in FIG. 2, the on-line reading is represented by:

$$O_2[\text{ppb}] = \text{cell current/calibration slope}$$

While the verification slope can be expressed as:

$$\text{slope} = \text{delta current}/20 \text{ ppb}$$

The Faraday verification does not provide a method for the calibration of absolute zero, instead, only provides a method of checking whether the slope is correct.

It is therefore an object of the present invention to provide a method for calibrating a dissolved oxygen analyzer that does not have the drawbacks or shortcomings of the conventional calibration methods.

It is another object of the present invention to provide a method for calibrating a dissolved oxygen analyzer that does not require the exposure of an oxygen electrode to the atmosphere and thus avoiding the oxidation of the silver electrode.

It is a further object of the present invention to provide a method for calibrating a dissolved oxygen analyzer that only requires the exposure of an oxygen electrode to a very low concentration of oxygen such that the lifetime of the silver electrode can be extended.

It is another further object of the present invention to provide a method for calibrating a dissolved oxygen analyzer that utilizes an oxidizer solution for the calibration of absolute zero.

It is still another object of the present invention to provide a method for calibrating a dissolved oxygen analyzer such that the lifetime of a silver anode utilized in an oxygen electrode can be at least doubled.

It is yet another object of the present invention to provide a dissolved oxygen analyzer which includes an oxidizer solution inlet and an oxidizer solution reservoir for determining an absolute zero point.

It is still another further object of the present invention to provide a dissolved oxygen analyzer which can be automatically calibrated by utilizing a saturated aqueous solution of sodium sulfite for determining the absolute zero point.

It is yet another further object of the present invention to provide a method for calibrating a dissolved oxygen analyzer by first setting a zero point on the analyzer by using an oxidizer solution and then setting a span point on the analyzer by filling a sample solution in the analyzer and flowing a cell current through a Faraday electrode until a 20 ppb oxygen is generated.

SUMMARY OF THE INVENTION

In accordance with the present invention, a method and an apparatus for the automatic calibration of a dissolved oxygen analyzer are provided.

In a preferred embodiment, a method for calibrating a dissolved oxygen analyzer can be carried out by first setting a zero point on the analyzer by filling a saturated aqueous solution of an oxidizer that contains zero ppb oxygen in the analyzer, and then setting a span point on the analyzer by filling a sample solution in the analyzer and flowing a cell current through a Faraday electrode until a quantity of oxygen that is not more than 10 ppb higher than an estimated oxygen content of the sample solution is obtained, and calculating a slope from the zero point and the span point.

In the method of calibrating a dissolved oxygen analyzer, the saturated aqueous solution of an oxidizer used may be a saturated aqueous solution of a compound that includes sodium sulfite ($Na_2SO_3$). The sample solution may be an ultrapure water, or any other solution that contains less than 100 ppb oxygen. The method may further include the step of providing a Faraday electrode mounted in the dissolved oxygen analyzer equipped with a silver anode and a gold cathode. The sample solution may be an ultrapure water that contains less than 50 ppb oxygen.

The present invention is further directed to a dissolved oxygen analyzer that includes an oxygen electrode that has a silver anode and a gold cathode, a Faraday electrode for performing electrolysis on a sample and for determining a span point, a sample inlet valve, an oxidizer solution inlet valve, an oxidizer solution reservoir for determining a zero point, and a sample outlet valve.

In the dissolved oxygen analyzer, the oxidizer solution reservoir stores a saturated aqueous oxidizer solution, or stores a saturated aqueous solution of sodium sulfite. The sample inlet valve and the oxidizer solution inlet valve are connected to a three-way valve for establishing fluid communication with the analyzer. The sample inlet valve admits a sample of ultrapure water that contains less than 100 ppb oxygen. The analyzer may further include a flow regulating valve positioned between the three-way valve and the Faraday electrode. The analyzer may further include an oxygen display and a Faraday display. The Faraday electrode performs electrolysis on ultrapure water producing oxygen and hydrogen gases.

In an alternate embodiment, a method for calibrating a dissolved oxygen analyzer can be carried out by the operating steps of providing a dissolved oxygen analyzer that is equipped with an oxygen electrode, a Faraday electrode, a sample inlet valve, an oxidizer solution inlet valve, an oxidizer solution reservoir, and a sample outlet valve; closing the sample inlet valve; opening the oxidizer solution inlet valve; flowing a saturated aqueous solution of the oxidizer into the analyzer; closing the sample outlet valve; setting a reading on the analyzer to zero when the reading is stabilized and establishing a zero point; flowing a sample solution into the analyzer; and flowing a current to the Faraday electrode until a 20 ppb oxygen is produced and setting the point as a span point for completing a two-point calibration process.

In the method for calibrating a dissolved oxygen analyzer, the oxidizer solution may be a saturated aqueous solution of $Na_2SO_3$ which contains zero ppb of oxygen. The method may further include the step of determining a slope from the zero point and the span point. The method may further include the step of flowing a sample solution of an ultra pure water that has less than 100 ppb oxygen. The method may further include the step of providing a Faraday electrode that is mounted in the dissolved oxygen analyzer equipped with a silver anode and a gold cathode. The method may further include the step of providing a sample solution of an ultra pure water that contains less than 50 ppb oxygen.

BRIEF DESCRIPTION OF THE DRAWINGS

These objects, features and advantages will become apparent by an examination of the following specification and the appended drawings in which.

DETAILED DESCRIPTION OF THE PREFERRED EMBODIMENT

The present invention discloses a method for calibrating a dissolved oxygen analyzer and an apparatus for carrying out the method that is equipped with an oxidizer solution reservoir.

The method for automatically calibrating a dissolved oxygen analyzer can be carried out by the major steps of first setting a zero point and then setting a span point on the analyzer. For instance, a zero point can be set on the analyzer by filling a saturated aqueous solution of an oxidizer that contains 0 ppb oxygen into the analyzer, while the span point can be set on the analyzer by filling a sample solution in the analyzer and flowing a cell current through a Faraday electrode until a quantity of oxygen that is not more than 10 ppb higher than the estimated oxygen content of the sample solution is obtained. The present invention novel method can further be executed by calculating a slope from the zero point and the span point.

A suitable oxidizer solution utilized in the present invention novel method may be any type of oxidizer solution, while a saturated aqueous solution of a compound that contains sodium sulfite ($Na_2SO_3$) may be particularly suitable. The present invention novel method can be used to detect dissolved oxygen content in any liquid and is particularly suited for determining a dissolved oxygen content in ultrapure water or DI water. For an ultrapure water, the amount of dissolved oxygen contained is normally less than 100 ppb, preferably less than 50 ppb and most preferably less than 10 ppb.

The present invention further discloses an apparatus for calibrating a dissolved oxygen analyzer automatically by a two-point calibration method utilizing a zero point and a span point. The apparatus produces a calibration with a substantially reduced error margin. The apparatus is provided with an oxidizer solution inlet valve, a three way flow control valve and an oxidizer solution reservoir. An oxygen electrode is included for measuring the oxygen content in ultrapure water by utilizing a Faraday electrode and conducting an electrolysis reaction to produce oxygen and hydrogen gases. The oxidizer solution reservoir provides a saturated aqueous solution of a strong oxidizer into a flow chamber such that the flow chamber reads 0 ppb oxygen for zeroing the oxygen reading in an oxygen display panel. The Faraday electrode is then utilized to generate an electrolysis reaction in a sample solution by flowing a current into the electrode that is sufficient to produce 20 ppb oxygen. The point obtained at the cell current and the 20 ppb oxygen is then taken as the span point. A two-point calibration method is thus completed with the determination of the two points and a slope that can be determined from the two points.

Figure 1:
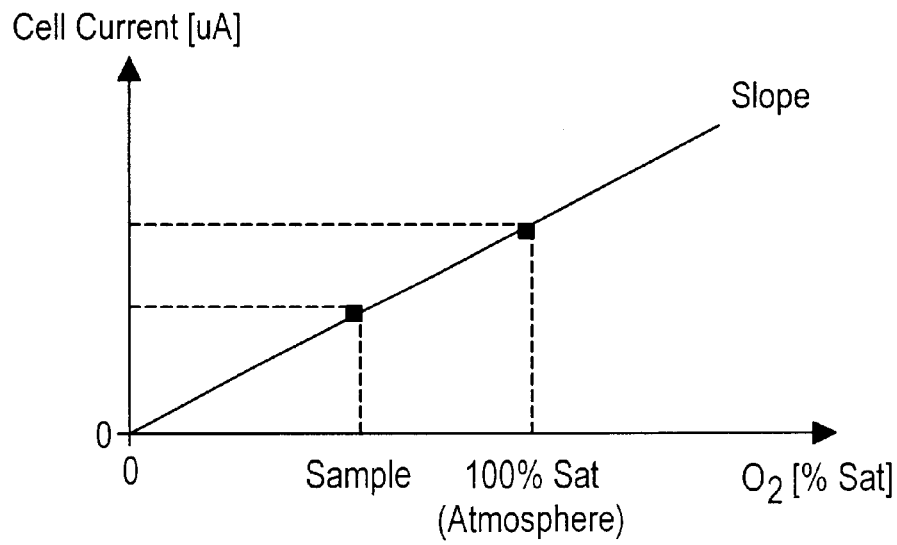
FIG. 1 is a graph illustrating a conventional method for calibrating a dissolved oxygen analyzer by using an air calibration method.
Figure 2:
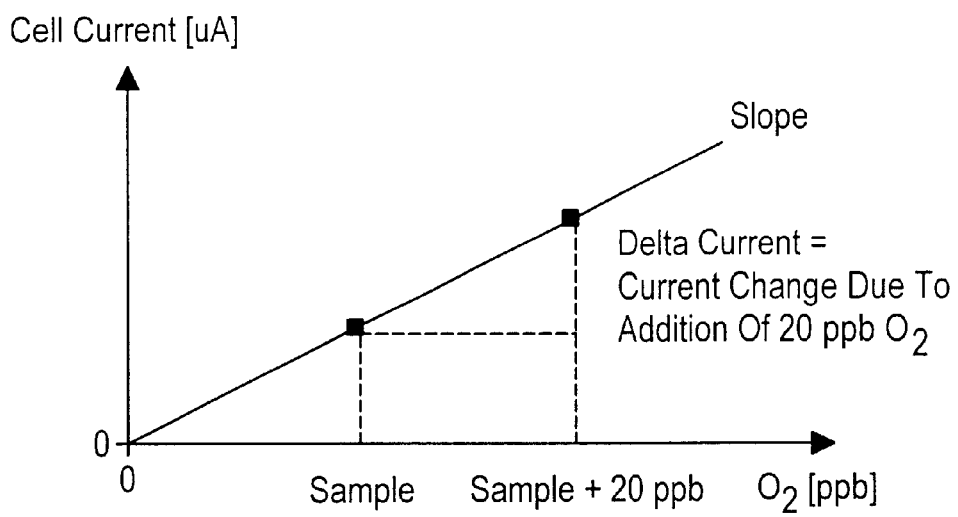
FIG. 2 is a graph illustrating a conventional method for calibrating a dissolved oxygen analyzer by using a Faraday verification method.
Figure 3:
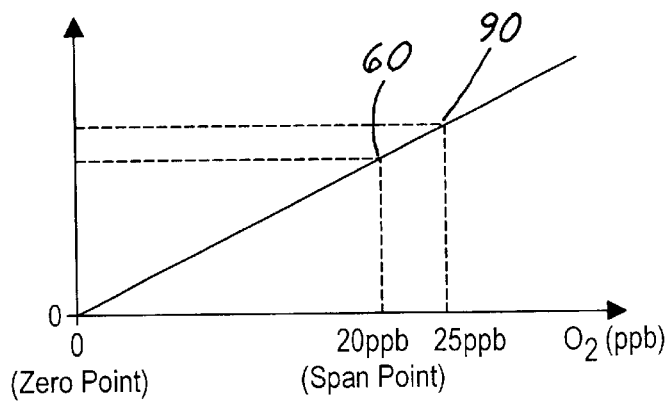
FIG. 3 is a graph illustrating the present invention method for calibrating a dissolved oxygen analyzer by first calibrating a zero point on an oxidizer solution and then calibrating a span point on a sample solution by producing 20 ppb or 25 ppb oxygen.
Figure 4:
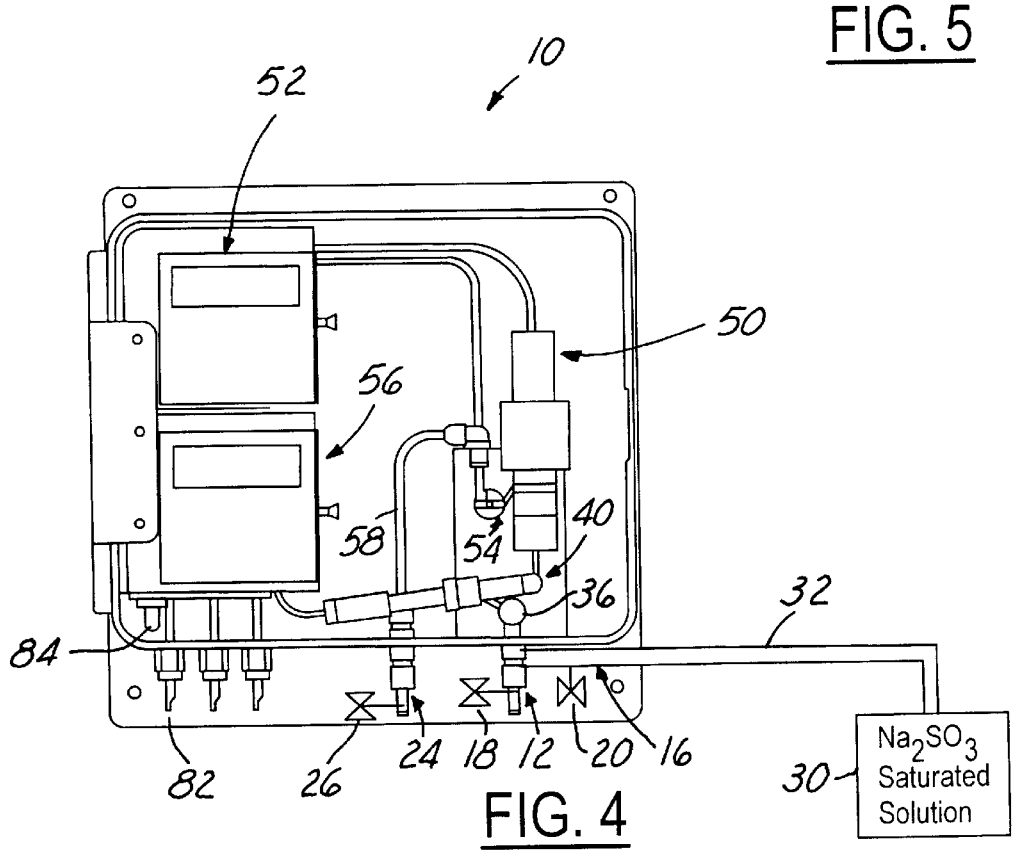
FIG. 4 is a side view of a present invention dissolved oxygen analyzer equipped with an oxidizer solution reservoir.

FIG. 3 is a graph illustrating the results obtained by the present invention novel method and apparatus, while FIG. 4 is a side view of the present invention novel apparatus 10 for conducting the automatic dissolved oxygen analysis. In the apparatus 10, a sample solution inlet 12 and an oxidizer solution inlet 16 which are controlled by inlet valves 18, 20 respectively are used. A sample outlet 24 and an outlet control valve 26 are further provided. An oxidizer solution reservoir 30 is provided for storing an oxidizer solution, i.e., a $Na_2SO_3$ aqueous solution. The aqueous oxidizer solution is fed to the oxidizer solution inlet 16 through conduit 32.

The apparatus 10 further includes a flow regulating valve 36 and a Faraday electrode 40 for conducting an electrolysis reaction on the sample solution that is flown in from the sample inlet 12. An oxygen electrode 50 is further provided for determining the oxygen content in the sample solution which is in fluid communication with the sample inlet 12. The oxygen content detected by the oxygen electrode 50 is displayed on an oxygen display panel 52, while the results obtained by the Faraday electrode 40 is displayed on display panel 56. A turbine wheel flow sensor 54 is utilized to indicate a flow of liquid through the sensor into conduit 58 and sample outlet 24 through the outlet control valve 26. The Faraday electrode 40 is utilized in the present invention novel apparatus 10 for calibration of the span point 60 shown in FIG. 3.

Figure 5:
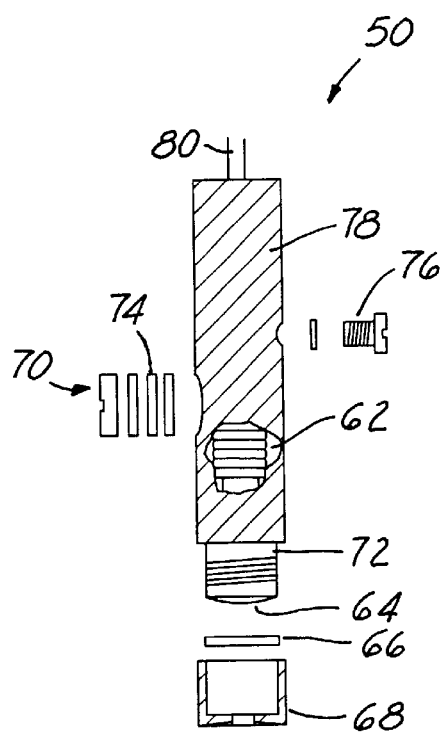
FIG. 5 is a cross-sectional view of an oxygen electrode utilized in the present invention dissolved oxygen analyzer.

A cross-sectional view of the oxygen electrode 50 is shown in FIG. 5. The electrode 50 consists of a silver anode 62, a gold cathode 64, a Teflon membrane 66 and a screw cap 68 for the electrode head 72. The oxygen electrode 50 further includes a pressure compensation screw 70, a pressure compensation membrane 74, a filling hole sealing screw 76 mounted in an electrode body 78 and an electrode cable 80 for sending a signal to the oxygen display panel 52. A power cord 82 and a power switch 84 are further included on the apparatus 10. The function of the oxygen electrode 50 can be described in the following manner. The driving force for the electron transfer reaction between $O_2$, $H_2O$ and Ag is the amperometric voltage across the electrodes of the gold cathode 64 and the silver anode 62. The voltage is supplied by the electronic amplifier (not shown). The current flowing through the cell is determined by the amount of oxygen reduced at the cathode and is directly proportional to the sample concentration. It has been found that the diffusion rate of oxygen through the membrane 66 is affected by temperature. A proper selection of the electrode's filling solution and the membrane material allows automatic temperature compensation of the electrode's output. During a calibration procedure of the present invention novel method, the sample solution temperature is continuously monitored with a thermistor (not shown) mounted inside the gold electrode 64.

To execute the present invention novel calibration method, the sample inlet valve 18 is first closed. The inlet valve 20 for the oxidizer solution, i.e., a saturated aqueous solution of $Na_2SO_3$, of any other strong oxidizer, is then opened to allow the saturated solution to flow into the oxygen electrode 50. The dissolved oxygen content in a saturated, aqueous solution of $Na_2SO_3$ is known as zero since all the oxygen has been consumed. After the saturated, aqueous solution of the strong oxidizer is flushed through the oxygen electrode 50, the sample outlet valve 26 is closed. A reading of the oxygen content is then taken on the oxygen display panel 52 when the reading is stabilized and no longer varies. This reading obtained is reset to zero as the zero point for the calibration curve shown in FIG. 3.

In the next step of the calibration process, a span point for use in the two-point calibration process is determined. A sample solution is first flown through the sample inlet 12 by opening the sample inlet valve 18 into the analyzer apparatus 10 and by flushing out the saturated aqueous solution of the strong oxidizer. A suitable current is then flown into the Faraday electrode to produce an electrolysis reaction in the sample solution. The magnitude of the current flown in is carefully selected such that an amount of 20 ppb oxygen is produced and that the point at 20 ppb and the cell current is determined as the span point 60. This is shown in FIG. 3. The span point 60 can then be used with the zero point to calculate a slope and to use for calibrating the previously obtained slopes. During the span point determination, a slightly larger than 20 ppb oxygen, i.e., 25 ppb as shown by span point 90, may also be used when the approximate value of the oxygen content in the sample solution is known.

The present invention novel method and apparatus produces a reliable zero point obtained on a calibration solution of saturated aqueous solution of $Na_2SO_3$. This is not previously possible by any of the conventional calibration methods. It is only with the present invention novel method that an absolute zero point can be reliably obtained.

Another benefit made possible by the present invention novel method and apparatus is the low consumption of the silver electrode utilized in the oxygen electrode 50. Since only a very low content of oxygen is exposed to the silver electrode, i.e., about 20 ppb oxygen when compared to the conventional method of exposing a silver electrode to the atmosphere, the silver electrode has a lifetime that is at least twice that previously achievable by the conventional method. For instance, in the present invention novel apparatus, a silver electrode may last between five and ten years instead of the usual lifetime of two years in a conventional test apparatus.

The conventional test method and apparatus determine a zero point when there is no current flowing through the analyzer. The zero point obtained by the conventional method therefore is not an absolute zero which may have suffered some shifting and thus affected its accuracy. This is in contrast to the present invention novel method in which an absolute zero is obtained by utilizing a calibration solution of $Na_2SO_3$ which contains 0 ppb oxygen.

The present invention novel method and apparatus for the automatic calibration of a dissolved oxygen analyzer have therefore been amply described in the above descriptions and in the appended drawings of FIGS. 3–5.

While the present invention has been described in an illustrative manner, it should be understood that the terminology used is intended to be in a nature of words of description rather than of limitation.

Furthermore, while the present invention has been described in terms of a preferred embodiment, it is to be appreciated that those skilled in the art will readily apply these teachings to other possible variations of the inventions.

The embodiment of the invention in which an exclusive property or privilege is claimed are defined as follows:

What is claimed is:

1. A method for calibrating a dissolved oxygen analyzer comprising the steps of:

setting a zero point on the analyzer by filling said analyzer with a saturated aqueous solution of an oxidizer that contains 0 ppb oxygen, setting a span point on the analyzer by first filling a sample solution in said analyzer and then flowing a cell current through a Faraday electrode until a quantity of oxygen that is not more than 10 ppb higher than an estimated oxygen content of the sample solution is obtained, and calculating a slope from said zero point and said span point.

2. A method for calibrating a dissolved oxygen analyzer according to claim 1, wherein said saturated aqueous solution of the oxidizer is a saturated aqueous solution of a compound comprising sodium sulfite ($Na_2SO_3$).

3. A method for calibrating a dissolved oxygen analyzer according to claim 1, wherein said sample solution is an ultrapure water.

4. A method for calibrating a dissolved oxygen analyzer according to claim 1, wherein said sample solution is an ultrapure water that contains less than 100 ppb oxygen.

5. A method for calibrating a dissolved oxygen analyzer according to claim 1, wherein said sample solution is an ultrapure water that contains less than 50 ppb oxygen.

6. A method for calibrating a dissolved oxygen analyzer comprising the steps of:

providing a dissolved oxygen analyzer equipped with an oxygen electrode, a Faraday electrode, a sample inlet valve, an oxidizer solution inlet valve, a reservoir for said oxidizer solution, and a sample outlet valve, closing said sample inlet valve, opening said oxidizer solution inlet valve, flowing a saturated aqueous solution of said oxidizer into said analyzer, closing said sample outlet valve, setting a reading on said analyzer to zero when said reading is established and thus establishing a zero point, flowing a sample solution into said analyzer, and flowing a current to said Faraday electrode until a 20 ppb oxygen is produced and setting said point as a span point for completing a two-point calibration process.

7. A method for calibrating a dissolved oxygen analyzer according to claim 6, wherein said oxidizer solution is a saturated aqueous solution of $Na_2SO_3$ which contains 0 ppb of oxygen.

8. A method for calibrating a dissolved oxygen analyzer according to claim 6 further comprising the step of determining a slope from said zero point and said span point.

9. A method for calibrating a dissolved oxygen analyzer according to claim 6 further comprising the step of flowing said sample solution of an ultrapure water containing less than 100 ppb oxygen.

10. A method for calibrating a dissolved oxygen analyzer according to claim 6 wherein said sample solution is an ultrapure water that contains less than 50 ppb oxygen.

* * * * *